United States Patent [19]

Steigelmann et al.

[11] 4,015,955
[45] Apr. 5, 1977

[54] FLUID SEPARATION PROCESS AND MEMBRANE

[75] Inventors: Edward F. Steigelmann, Naperville, Ill.; Charles S. Sokol, Cincinnati, Ohio

[73] Assignee: Standard Oil Company, Chicago, Ill.

[22] Filed: Feb. 5, 1975

[21] Appl. No.: 547,217

[52] U.S. Cl. .............................. 55/16; 260/677 A
[51] Int. Cl.² .................. C07C 11/12; C07C 9/00
[58] Field of Search ........... 210/22, 23; 55/16, 158; 260/677 A

[56] References Cited

UNITED STATES PATENTS

| | | | |
|---|---|---|---|
| 3,758,603 | 9/1973 | Steigelmann et al. | 55/16 X |
| 3,773,844 | 11/1973 | Perry et al. | 260/677 A X |
| 3,801,666 | 4/1974 | Blytas | 260/677 A |

Primary Examiner—Frank A. Spear, Jr.
Attorney, Agent, or Firm—Morton, Bernard, Brown, Roberts & Sutherland

[57] ABSTRACT

There is described an improved separation membrane-liquid barrier system of the type containing complex-forming, metal-containing ionic components, and an improved separation process in which the membrane-liquid barrier is employed. The membrane is in contact with an aqueous liquid barrier containing cuprous ions, such as a cuprous salt or a cuprous salt complex, e.g. a CuCl complex, preferably a $CuCl-NH_4Cl-HCl$ complex, and the barrier is in contact with a reducing agent that retards the complexing $Cu^+$ ion from being oxidized to $Cu^{+2}$. The reducing agent is relatively stable when positioned in the membrane and is not unduly oxidized by air nor does it unduly interfere with the essential function of the cuprous ions during the separation process. Elemental copper may function as a reducing agent that retards oxidation of $Cu^+$ ion to $Cu^{+2}$. The liquid barrier containing complex-forming cuprous ions can be subjected to a strong reducing agent during the separation process to reduce some of the cuprous ions to elemental copper.

23 Claims, No Drawings

FLUID SEPARATION PROCESS AND MEMBRANE

This invention is directed to separation systems, preferably olefin separation systems, in which a semi-permeable membrane is employed in contact with a liquid barrier containing a complex-forming, metal-containing ionic component. The liquid barrier has in solution therein cuprous ions which may be in complex form, and the complex may contain, for example, ammonium ions and a mineral acid such as hydrochloric acid as part of the complex-forming ionic component. In this invention, the liquid barrier is in contact with a reducing agent in an amount sufficient to retard oxidation of $Cu^+$ ions which results in improved, prolonged performance of the membrane-liquid barrier system. The reducing agent is relatively stable when positioned in the system, is not unduly oxidized by air (oxygen), and does not unduly interfere with the essential function of the $Cu^+$ during the separation process. The reducing agents may include elemental copper, sulfates, oxalates, sulfites, arsenites and other agents as more fully set forth below. The reducing agents may be included the liquid barrier in any desired manner, for example, they may be added to the membrane during its preparation and thereby be included in the liquid barrier when it contacts the membrane. The reducing agent may alternatively or additionally be added to the liquid barrier during operation of the separation process, and thus the agent may be added to the system along with the feed material which undergoes separation.

There is considerable commercial interest in separating materials, e.g. aliphatically-unsaturated hydrocarbons, from fluid mixtures containing them. The aliphatically-unsaturated hydrocarbons are reactive materials that serve in various roles in chemical syntheses. A number of the unsaturated hydrocarbons are employed as monomers in the formation of polymers and, in this regard, olefins such as ethylene, propylene, butadiene and isoprene are well known. These olefins, as well as other unsaturated materials, for instance, acetylene, are also used to form relatively low molecular weight products.

The aliphatically-unsaturated hydrocarbons are most often made available on a commercial basis in admixture with other chemical compounds, frequently other hydrocarbons. These unsaturated hydrocarbon-containing streams are usually by-products of chemical syntheses or separation processes. When the hydrocarbon streams are liquid under normal conditions or can readily be made so, ordinary distillation techniques can be used to separate the hydrocarbon components providing they have sufficiently different boiling points for the process to be economically feasible. Especially when the hydrocarbon mixtures contain materials having close boiling points, which is frequently the case with hydrocarbons of the same number of carbon atoms or having a difference of only one carbon atom, distillation may not be an attractive separation procedure. In such cases, more expensive processes are often used and involve operations such as solvent extraction or extractive distillation which entail considerable expense, if indeed they are technically feasible in a given situation.

When the mixture containing the aliphatically-unsaturated hydrocarbon is essentially in a gaseous state at normal or ambient conditions of temperature and pressure, separation of the desired component from the mixture may be even more troublesome. In these situations, cryogenic processes may be used, but they are expensive. The components of these normally gaseous mixtures may not even have particularly close boiling points, but, nevertheless, the mixture must be cooled in order to separate one or more of its components. In spite of the considerable cost of cryogenic operations, the procedure has been employed commercially for the separation of ethylene from other gaseous materials such as ethane and methane.

Systems are now known which are directed to methods for separation various materials from mixtures containing them, and involve the combined use of liquid barrier permeation and metal complexing techniques which can exhibit high selectivity factors. In the processes, the liquid barrier is an aqueous solution having dissolved therein complex-forming, metal-containing ions which will complex with the component to be separated, and the liquid barrier is employed in contact with a semi-permeable membrane which is essentially impermeable to the passage of liquid. Preferably, the liquid barrier containing the complex-forming ions is at least partially within a hydrophilic, semi-permeable film membrane. When operating in this manner, there may be no need to maintain contact of the film with a separate or contiguous aqueous liquid phase during the process, which may facilitate the use of a greater variety of semi-permeable members as far as physical configuration is concerned. Thus, the membranes can be designed without having to provide a separate liquid phase adjacent the film, and this may enable the use of film configurations having a greater surface or contact area. The membranes employed are fairly stable, have satisfactory permeability and exhibit good selectivity for separating various complex-forming materials, e.g. aliphatically-unsaturated hydrocarbons.

In other systems for conducting the separations, the aqueous liquid is disposed, at least partially, as a distinct liquid phase, contiguous to and on the feed side of the semi-permeable membrane film, wherein the mixture to be separated is introduced into the liquid phase. Alternatively, the aqueous liquid phase has been held in contact with a semi-permeable membrane film by absorbing the liquid in a porous, inert, solid matrix such as filter paper, and holding the wet paper next to the semi-permeable membrane in, for instance, a sandwich-type cell construction.

In each of these systems, the liquid phase employed may have cuprous ions in the metal-containing complexing component. Often, the cuprous ions are present in a complex, and, for instance, they may be combined with ammonium ions to provide copper ammonium complex ions which are active to form a complex with the material to be separated by use of the membrane. Preferably, approximately equimolar amounts of cuprous ions and ammonium ions are used, but either type of ions may be in excess. The ammonium ions can be provided in various convenient ways, preferably as an acid salt such as ammonium chloride or as ammonium hydroxide or ammonium carbonate. In order to enhance the selectivity of the copper ammonium ion complex in the separation process, the membrane film, and thus the liquid barrier solution, may be made more acidic, by, for instance, providing a water-soluble acid such as a mineral acid, especially hydrochloric acid, in the film or liquid barrier solution. Preferably, the pH of the liquid barrier in this form of the invention is below about 5 with the acid in the solution.

While the cuprous ion based, complex-forming components are workable separation materials, they have been less effective than, for example, the more expensive noble metal salts such as silver nitrate. The added expense of employing such salts as silver nitrate instead of the copper salt based complexes has been compensated for by the increased yield and selectivity achieved with the noble metal salts.

This invention is directed to cuprous-ion based, complex-forming component-containing liquid barrier membrane systems which obtain improved performance, and to the separation processes in which such systems are used. In a cuprous ion-containing liquid barrier membrane system, as the separation proceeds, the cuprous ions are oxidized to cupric ions by oxygen (air) or other oxidizing agent which may enter the system with the material to be separated, or by other means. The selectivity and separation ability of the system decreases significantly as the cuprous complexing ions are oxidized to the cupric state. However, in the process of this invention, the addition of small but effective quantities of reducing agent retards this oxidation and sustains membrane-liquid barrier system performance over prolonged periods of use. The novel membrane-liquid barrier systems of this invention generally comprise a semi-permeable film in contact with a liquid barrier containing in solution a cuprous ion based complex-forming component, and the barrier is in contact with a reducing agent which retards the oxidation of cuprous ($Cu^+$) ions to cupric ($Cu^{++}$) ions which complex less readily with the material to be separated. The reducing agent is used in an amount sufficient to retard the oxidation of cuprous ions, thereby resulting in stabilization of the complex-forming ionic material and significant improvement in performance in the separation procedure.

The processes of the present invention employing the complex-forming cuprous ion-containing liquid barrier and the reducing agent in contact with a semi-permeable membrane are advantageously used to separate aliphatically-unsaturated hydrocarbons, and the reducing agent serves to retard oxidation of the metal-containing ions and enhances membrane selectivity which results in superior processes which may be carried out at high capacities over prolonged periods of time. In addition, the separation processes of this invention are less costly than those without the reducing agent, and effective use of the reducing agent in the liquid barrier may require considerably less frequent shut-downs of the process for membrane reactivation, and complex-forming copper component material costs are correspondingly decreased. In addition, due to the improved performance of the membrane systems of this invention, separation processes may be successfully performed without the use of more expensive salts such as silver nitrate. Also, unlike the noble metal salt-containing separation procedures, the membrane systems of this invention are not poisoned by, and may advantageously be used in, acetylene separation operations.

The various water-soluble cuprous salts may be used as the base material for the complex-forming component of the liquid barrier of this invention, but the cuprous material is preferably a halogen salt, particularly copper chloride (CuCl). Generally, a minor amount say from about 1 to about 30%, preferably from about 5 to about 25%, by weight of cuprous salt based on the salt-free liquid in the liquid barrier, is used. These salts may be combined with ammonium ions, and, in addition, a mineral acid component may also be used, as discussed above. A particularly preferred cuprous salt-ammonium compound-mineral acid complex for use as the complex-forming component in the membrane-liquid barrier system is the cuprous chloride-ammonium chloride-hydrochloric acid complex (CuCl—NH$_4$Cl—HCl). Liquid barriers of this invention containing the cuprous salt-ammonium compound complex generally contain from about 25 to about 40%, preferably from about 50 to about 200%, by weight of the ammonium compound, based on the weight of the cuprous salt. Additionally, the liquid barrier may contain mineral acid, such as hydrochloric acid, in an amount, for example, from about 0.5 to about 130%, preferably from about 3 to about 70%, by weight of mineral acid based on the weight of the cuprous salt.

The reducing agent employed in contact with the liquid barrier in the present invention is one that is relatively stable when positioned in the membrane or in the liquid barrier, is not unduly oxidized by air (oxygen), and does not unduly interfere with the complexing reaction involving the material to be separated. The reducing agent may be soluble or insoluble in water, and a particularly useful reducing agent is elemental copper. The reducing agents include sulfates such as Mohr's reagent (ferrous ammonium sulfate: $(NH_4)_2SO_4 \cdot Fe_2(SO_4)_3$), and cerrous sulfate, other cerrous salts, oxalate salts such as those of oxalic acid ($H_2C_2O_4$), stable sulfites such as sodium bisulfite (NaHSO$_3$), stable thiosulfates such as sodium thiosulfate ($Na_2S_2O_3$), stannous chloride, arsenite salts such as sodium arsenite (NaAsO$_2$), sulfur dioxide and other reducing agents.

The amount of reducing agent in contact with the liquid barrier to stabilize the complex-forming solution may depend upon the extent of exposure of the complex-forming solution to oxidizing agents. Often a minor amount of reducing agent may be used, e.g. say at least about 0.05 to about 50%, for example, about 2 to about 40%, and preferably about 5 to about 25%, by weight, based on the weight of the complex-forming solution. The reducing agent may be supplied to the separation system by direct or indirect addition to the liquid barrier. Thus, the reducing agent may be placed in the membrane or in the feed material undergoing separation. These additions may be made periodically or continuously to regenerate or maintain the stability of the complex-forming ions. The amount of reducing agent used is generally sufficient to maintain or regenerate the complex-forming ions, and this may be determined by monitoring the separated product and adding reducing agent to the system until separation is at the desired level of selectivity or yield. Additionally, the reducing agent may be passed through the membrane-liquid barrier system and may be regenerated by chemical or electrolytic reduction and subsequently recycled.

In those embodiments in which elemental copper is employed as a reducing agent, the liquid barrier used in the membrane-liquid barrier system may be in contact with, in addition to the elemental copper, a permeability enhancing component, for example, t-butandol or tetrafluoroboric acid. The permeability enhancing component can be used in a minor amount, e.g., from about 0.01 to about 10%, preferably from about 0.1 to about 2%, by weight based on the weight of the complex-forming cuprous ion-solution. The permeability-enhancing compound may be included in the liquid barrier solution employed in initial preparation of the barrier-membrane system or it may be delivered to the liquid barrier during the separation process.

In accordance with this invention, contact of the semi-permeable membrane and the aqueous liquid barrier may be provided in various ways, such as those mentioned above. In one embodiment the system has at least a portion of the aqueous barrier within the membrane, and this can be accomplished by impregnation of the membrane with an aqueous solution containing the complex-forming cuprous ions. By using a differential pressure across the film, impregnation with the liquid barrier may be enhanced, but one must be careful not to rupture or otherwise deleteriously affect the physical integrity of the membrane film. The complex-forming copper ions may be placed within the membrane of this invention by forming the film from a liquid solution containing both the film-forming material and the complex-forming cuprous ion component. Thus, the film-forming solution may contain liquid solvent which may include water, liquid organic or inorganic solvent or combinations of such materials. The solvent may be formulated so that the film-forming material and complex-forming cuprous ion component will be soluble in the liquid phase to provide a relatively homogeneous film-forming composite. This solution can then be used to make the essentially solid, semi-permeable, polymer membrane by an appropriate film-forming technique such as casting. In this embodiment the reducing agent may be included with the solution containing both the film-forming material and the complex-forming metal component, or the reducing agent may subsequently be added to the cast membrane.

In those instances in which film-forming constituents may be detrimental to the reducing agent or in which the film-forming constituents may be detrimentally affected by the reducing agent, the reducing agent may be added to the film membrane after it has been formed. This procedure may apply, for example, in some instances where a solvent other than water is employed for dissolving the film-forming constituents. However, because cuprous salts such as cuprous chloride and the like are readily oxidized, it is preferred that the reducing agent be included in the flim-forming solution along with the complex-forming conponent. Even when the complex-forming component is not included in the film-forming solution, it may be desirable to include the reducing agent in the solution. Alternatively, the complex-forming cuprous ion component may be included with the film-forming constituents and the resulting formed film membrane may be stored in a dry state and subsequently wetted before use. In this case, it may be desirable to include the reducing agent in the wetting solution in an effective amount, although it may be preferred to be included in the original film-forming solution.

In another embodiment of the separation process employing the cuprous ion-containing liquid barrier-semi-permeable membrane system, the liquid barrier is subjected to a reducing agent in an amount and of sufficient strength to reduce some of the cuprous ions and produce elemental copper. The resulting copper acts as a reducing agent and retards oxidation of the complexing cuprous ions to cupric ions which do not readily complex with material to be separated. In addition to reducing some of the cuprous ions to elemental copper, the relatively strong reducing agent may also reduce any cupric ions which may be present to cuprous ions or elemental copper.

The membrane-liquid barrier systems containing a cuprous ion component which includes an elemental copper reducing agent may be provided without the addition of elemental copper powder. The method involves establishing a cuprous ion-containing liquid barrier, e.g. a $CuCl-NH_4Cl-HCl$ component, and subjecting the liquid barrier to a strong reducing agent which reduces some of the cuprous ions to elemental copper. The elemental copper may be produced before the liquid barrier membrane system is used, and may be produced during the process by either intermittently or continuously subjecting the membrane to a strong reducing agent which maintains the desired elemental copper level. The reducing agent may be used in an amount sufficient to reduce some of the cuprous ions to elemental copper and, in so doing, may reduce cupric ions to cuprous ions and/or elemental copper. The reducing agent may be fed to the membrane-liquid barrier during use in the separation process, for example, in the feed charged to the separation process, although the reducing agent may be provided in the membrane-liquid barrier in any suitable manner.

The relatively strong reducing agents which may be used in the present invention may be reducing agents which: (1) are stable in the liquid barrier; (2) are not oxidized by air (oxygen); (3) do not interfere with the $Cu^+$ complexing reaction; and (4) are strong enough to reduce cuprous ions to elemental copper to produce sufficient elemental copper in the liquid barrier to retard oxidation of the remaining cuprous ions. Among the strong reducing agents useful in the present invention are $NaBH_4$, $NaBH_3CH$, $NH_3$, $Ha_3N$, acidified $NH_2OH$, $NaH_2PO_2$ and $Na_2S_2O_4$.

The cuprous ions which are reduced to elemental copper may be those which were initially employed within the membrame-liquid barrier system as cuprous ions. Thus, the process may be performed with the cuprous ion-containing liquid barriers of the systems of the prior art, particularly cuprous salt-containing liquid barriers such as the $CuCl$ and the $CuCl-NH_4Cl-HCl$ complex-containing liquid barriers. Alternatively, the cuprous ions to be reduced may be those resulting from the oxidation of elemental copper reducing agent initially employed in the liquid barrier as described above, particularly the liquid barriers containing cuprous salts, such as the $CuCl$, $CuCl-NH_4Cl$ and the $CuCl-NH_4Cl-HCl$ complex-containing liquid barrier-membrane systems.

The elemental copper, if used, may be established within the cuprous ion-containing liquid barrier by the action of a strong reducing agent of the type described above to reduce some of the copper ions to elemental copper. In one process the temperature and strong reducing agent concentration are controlled so as to yield colloidal or slightly larger sized copper metal particles. The small particle size tends to increase the efficiency of the copper metal to retard oxidation of the cuprous ions to cupric ions and to reduce any cupric ions that are formed back to cuprous ions. However, the particles should not be so small that undue surface oxidation of the copper to $CuO$ would result from any oxygen which may pass through the membrane during use.

As mentioned, copper, as a mild reducing agent, may be included in contact with the liquid barrier, and thus may be included in the complex-forming component-film-forming solution. The mild reducing agent may be elemental copper which is produced by subjecting the cuprous ion-containing liquid barrier to a strong reducing agent after the membrane film is cast and the cuprous ion-containing liquid barrier established. For example, a CuCl—NH$_4$Cl—HCl solution may be impregnated into a cast polymer semi-permeable membrane film and the strong reducing agent may be passed through the member to reduce some of the cuprous ions to elemental copper. Reduction is usually performed until the desired elemental copper particles are established. The particle size may be governed by maximizing cuprous ion oxidation retardation on the one hand, and retardation of oxidation of the copper to CuO on the other hand. Generally, it is desirable to have particle sizes ranging from about 0.01 to about 4 mils, preferably from about 0.05 to about 3 mils. When these particles are formed, usually from about 0.05 to about 20%, preferably from about 2 to about 10%, by weight of the total dry cuprous salt initially contained in the liquid barrier is reduced to elemental copper.

In the system of the present invention, the amount of complex-forming ion in the liquid barrier may vary considerably, but is sufficient to accomplish the desired separation. Often, the complex-forming metal is provided in the membrane. This is a minor amount, say, about 1 to 50 weight percent, of the weight of the membrane on a non-aqueous basis, preferably about 5 to 25 weight percent. A suitable procedure for placing the solution of complex-forming ion in the semi-permeable film is by contacting the film with the solution, preferably including the reducing agent, and exerting a differential pressure across the solution and film. Thus, the present behind the solution is greater than that on the opposite side of the film, and as a result, the solution is forced into the film under pressure. Conveniently, the pressure on the solution is above atmospheric, and the opposite side of the film is essentially at atmospheric pressure. The pressure differential need not be large, for instance, it may only be at least about 5 or 10 and it should not be so great that the film is ruptured. This procedure could also be used to reactivate films which have been used for long periods of time to the point to where they have lost selectivity when used to perform the separation.

The membrane containing the complex-forming ions, with or without the reducing agent, may be handled and transported in an essentially non-aqueous form with or without the reducing agent, or with some water therein, for instance, an insufficient amount of water to be effective in the separation. In such case, water, with reducing agent where desired, may be added to the system to give a film in contact with sufficient water to be useful in performing the separation process of the invention. During use of the membrane, the amount of water present is preferably that which gives a substantial distinct or separate aqueous phase on the feed inlet side of the membrane. The film membrane can be wetted initially, and if it has a tendency to dry during use, additional water, with or without the reducing agent, can be placed in the film while it is used on-stream in the separation process of this invention, for instance, by inclusion of moisture in the feed charged to the system. Alternatively, but less advantageously, the operation can be stopped for addition of water and/or reducing agent to the system. In any event, care should be taken to insure that the film membrane during use is not so dry that it will exhibit non-selective permeability to the material to be separated from the feed, and will thereby not serve to separate a product having an increased concentration of the desired ingredient.

The concentration of the complex-forming ions in the film or liquid barrier may be rather low and still be sufficient to provide an adequate complexing rate so that excessive amounts of the semi-permeable membrane surface will not be needed to perform the desired separation. Conveniently, the concentration of the complex-forming ions in the aqueous forming the liquid barrier is at least about 0.1 molar and is preferably about 0.5 to 12 molar.

The liquid barrier employed in this invention is aqueous and may be composed of water or water and other liquids which are water-miscible. The amount of water in the liquid barrier employed in this invention may be a minor portion of the liquid phase, but preferably is a major portion or even essentially all of the liquid, on a reducing agent-free, salt-free basis. Thus, small or minor amounts of water, say as little as about 5 weight percent, on such basis in the liquid phase may serve to provide significant transport for the material to be separated across the liquid barrier. Generally, there may be at least about 5 weight percent liquid in the system, based on the dry weight of the membrane film but it is preferred that sufficient liquid be present to completely saturate the membrane film to assure the presence of excess complex-forming ions in the system. Any liquid present in the barrier in addition to water is preferably water-miscible and should be chosen as not to have a substantial deleterious effect on the separation to be accomplished. The liquid barrier may also contain a hygroscopic agent, e.g., in a minor amount, to improve the wetting or hydrophillic properties of the liquid and provide better contact with the feed.

The membrane films employed in the process of this invention include those which have been used in conjunction with complex-forming metal solutions, see for instance U.S. Pats. Nos. 3,758,603 and 3,758,605, incorporated herein be reference. Preferably, the films are of the essentially water-insoluble, hydrophilic, semi-permeable type. A membrane may be considered hydrophilic if it absorbs at least about 5 weight percent of water when immersed in distilled water for one day at room temperature and pressure. In the absence in the film of the liquid containing the complex-forming ions, the film is generally not adequately selective with respect to the passage of or permeation by the material to be separated to perform the desired separation at the desired rate. The film is generally essentially impermeable to liquids. Often, the film is permeable to essentially all of the components in the feedstock used in this invention when in the gaseous state. However, by having the film in contact with sufficient aqueous liquid to form a barrier, the simple diffusion of gas through the film is reduced or prevented, and the components of the feed stream must, therefore, traverse the film primarily by becoming part of, and then being separated from, the aqueous liquid phase in contact with the film. Thus, in the absence of the complex-forming ions in the aqueous medium, there could be a slight separation effected by the use of water as the liquid membrane since the individual components in the feed may exhibit differing solubilities in water. In the method of the present invention, however, the selectivity of the separation is greatly increased due to the presence of the complex-forming ions in the aqueous barrier medium.

Also, during use in the process of this invention, the liquid barrier is a sufficient amount so that adequate complex-forming ions are in solution, or at least react as if they are, to perform the desired separation.

Among the film-forming materials which may be employed in the present invention are the types that have heretofore been used for separation or purification of various chemical materials. Among these are the film-forming materials disclosed in U.S. Pats. Nos. 3,228,877 and 3,566,580, incorporated herein by reference. Advantageously, the materials can be employed to provide one component of the semi-permeable film membranes used in the present invention are those having a polyamide as an essential constituent. The polyamide film-forming materials are generally known and have also been designated as nylons. These polymers are characterized by having amide groups serving as recurring linkages between carbon chains in the product structure, and the polymers may be made by several procedures. Commonly, the polyamides are formed by reacting a polyamide and a dicarboxylic acid or its derivative such as an ester, especially a lower alkyl ester having, for instance, about 1 to 4 carbon atoms in each ester group. Other reactions which may be employed to form the polyamides include the self-condensation of monoamino, monocarboxylic acids and the reactions of cyclic lactams. In any event, the polyamide products contain recurring amide groups as an integral part of the principal polymer chain. The polyamides are described, for instance, in the Kirk-Othmer, *Encyclopedia of Chemical Technology*, Second Edition, Volume 16, beginning at page 1, Interscience Publishers, New York, 1968. Among the typical structural formulas of the linear polyamides are $H_2NRNH(COR'CONHRNH)_nCOR'COOH$ and $H_2NRCO(NHRCO)_nNHRCOOH$, where R and R' represent primarily carbon-to-carbon chains between functional groups in the reactants, and n represents the degree of polymerization or the number of recurring groups in the polymer chain. The polyamides which can be used in this invention are generally solid at room temperature, and have a molecular weight which makes them suitable for forming the desired film membranes. Polyamides of this type are described in, for instance, U.S. Pat. No. 3,355,409.

The carboxylic acids which may be used in forming the polyamides have an acyloxy group (—R—COO—) in their structure and the R member of this group is composed essentially of carbon and hydrogen and often contains about 6 to 12 carbon atoms. Such groups may be aliphatic, including cycloaliphatic, aromatic, or a mixed structure of such types, but the groups are preferably aliphatic and saturated with respect to carbon-to-carbon linkages. These R groups may preferably have straight chain carbon-to-carbon or normal structures. Among the useful dicarboxylic acid reactants are adipic acid, sebacic acid, azelaic acid, isophthalic acid, terephthalic acid, and the methyl esters of these acids.

The polyamides employed in making the polyamide film-forming membranes generally have at least two non-tertiary, amino nitrogen atoms. These nitrogen atoms may be primary or secondary in configuration, although amines having at least two primary nitrogen atoms are preferred. The polyamines may also have both primary and secondary nitrogen atoms and the polyamines may contain tertiary nitrogen atoms. The preferred polyamine reactants have aliphatic, including cycloaliphatic, structures, and often have from 2 to about 12 carbon atoms. Also, the preferred polyamines are saturated and have straight-chain structures, although branched-chain polyamines can be used. Among the useful polyamines are ethylene diamine, pentamethylene diamine, hexamethylene diamine, diethylene triamine, decamethylene diamine and their N-alkyl substituted derivatives, for instance, the lower alkyl derivatives which may have, for instance, 1 to 4 carbon atoms in each alkyl substituent.

Film-forming polymers which can be employed with special advantage in this invention are those in which the film-forming polyamide is an N-alkoxyalkyl-substituted polyamide. Materials of this type are well known, as shown, for instance, by U.S. Pats. Nos. 2,430,910, and 2,430,932, which disclose N-alkoxymethyl polyamides made by the reaction of a polyamide polymer, formaldehyde and alcohol. Generally, at least about 5% of the amide groups of the polymer are substituted with alkoxyalkyl groups and such substitution may be up to about 60% or more. Preferably, this substitution is about 10 to 15% with the product being soluble in hot ethanol.

The alcohols employed in making the N-alkoxyalkyl polyamides are generally monohydric and may have, for instance, from 1 to about 18 or more carbon atoms. The lower alkanols are preferred reactants, especially the lower alkanols having 1 to 4 carbon atoms. Among the useful alcohols are methanol, propanols, butanols, oleyl alcohol, benzyl alcohol, lauryl alcohol and alcohol ethers, for instance, the alkyl ethers of ethylene glycol.

The N-alkoxyalkyl polyamides which can be employed as film-forming materials in the present invention to provide the desired semi-permeable membrane may be reacted with cross-linking agents. Such agents may be, for example, polycarboxylic acids, especially the dicarboxylic acids which may have, for instance, from 2 to about 12 carbon atoms. Useful acids include oxalic acid, citric acid, maleic acid, and the like.

Film-forming membranes which can most advantageously be employed in the present invention can be made by intimately mixing, by either physical means or through chemical reaction, the N-alkoxyalkyl polyamide and a hygroscopic polymer material as described above, e.g., the water-soluble polyvinyl alcohols. The polyamides and hygroscopic polymer may be used as a physical admixture or in various reacted forms, for instance, as cross-linked polymers or block or graft copolymers. It is preferred that at least one of the polymers be cross-linked. The hygroscopic polymer may be employed in an amount sufficient to enhance the hydrophilic properties of the polyamide and may generally be up to about 75 weight % or somewhat more of the composition based on the total polyamide and hygroscopic polymer, and the latter is often at least about 5 or 15% if its presence is sufficient to impart a significant property to the film-forming combination. Preferably, each of the hygroscopic polymer and the polyamide are about 25 to 75% of their combination or total amount, or the hygroscopic polymer may be about 35 to 55% and the polyamide about 45 to 65% of their combination. The mixed N-alkoxyalkyl polyamide and hygroscopic polymer composition may also be formed into a film membrane and then the complex-forming ion added, e.g., by impregnation of the film. The resulting metal-containing membrane can be used in the separation procedures.

The polyvinyl alcohols which can be employed in the membranes used in the present invention are essentially water-soluble materials, at least in hot water, and many of these are commercially available. The molecular weights of these polymers are often at least about 1000, and the commonly in the range of about 10,000 to 300,000. Suitable polyvinyl alcohols are described in, for example, "Water-Soluble Resins", Second Edition, Edited by Robert L. Davidson and Marshall Sittig, pages 109 to 115, Reinhold Book Corporation, New York, N.Y. The polyvinyl alcohol may be cross-linked, especially after the membrane is formed from the polymeric materials. The presence of the cross-linked polyvinyl alcohol may increase the strength of the membranes and increase their resistance to loss of polyvinyl alcohol by leaching during use. The cross-linking agents used may be polycarboxylic acids, preferably those having from 2 to about 12 carbon atoms. The useful acids are preferably water-soluble; and among the polycarboxylic acids, the diacids and triacids, and especially the saturated diacids, are preferred. Included among these are the aliphatic polycarboxylic acids, including oxalic acid, citric acid, maleic acid, malonic acid, and the like. The polyvinyl alcohol may also be cross-linked by reaction with formaldehyde, e.g., by immersing the fibers in an aqueous bath containing 40% $(NH_4)_2SO_4$, 10% NCHO and 7½% $H_2SO_4$, at 50° C. for 1 to 3 hours.

In another method of cross-linking the polyvinyl alcohol, the formed membranes may be combined with the cross-linking agent and the composite can be subjected to heat treatment to effect cross-linking. The temperatures used during cross-linked should be sufficient to enhance the cross-linking reaction to the desired degree, but not such as to affect the fibers detrimentally. The amount of cross-linking agent used may depend upon which agent is chosen, the amount and molecular weight of the polyvinyl alcohol present in the mixture, and the degree of completion of the cross-linking reaction desired. The amount of cross-linking agent generally used may be from about 1 to about 100 weight percent, and preferably from about 5 to about 60 weight percent, based on the weight of the polyvinyl alcohol.

Cross-linking of the N-alkyloxyalkyl polyamides can be accomplished by contact of the membranes with an organic or inorganic acidic catalyst such as a sulfonic acid of an aromatic hydrocarbon, mild nitric acid and the like. Such catalysts may, for instance, be naphthalene or toluene sulfonic acids, and cross-linking can be accomplished at elevated temperatures. During contact of the membrane with the acid catalyst as an aqueous solution, it is preferred that a water-soluble alkali metal salt be dissolved in the solution to maintain the integrity of the polyvinyl alcohol by reducing its tendency to dissolve in the aqueous catalyst solution. Cross-linking or other modification of the polymer composition may be effected before, during or after it is formed into the shape in which it is going to be used, but if this occurs before shaping, the modification should not be so extensive that the desired shaping may not be accomplished.

The film membranes which can be employed in this invention are preferably self-supporting and have sufficient strength not to require any additional supporting material on either of its sides during use. With some films, however, it may be necessary, advantageous or convenient to provide adequate support such as additional film or sheet-like materials on one or both sides of the film membrane. These supporting structures are frequently very thin materials and may be permeable to both liquids and gases and not serve a separating function with respect to any component of the feed stream. Alternatively, the supporting film may be permeable to gases, but not to liquids.

The film membranes may be in the form of flat disclike films, for example, or may be extruded membranes in the form of thin hollow fibers. In flat form, the film membranes may have a thickness of up to about 30 mils or more. Preferably, the thickness is up to about 10 or 15 mils. The films are sufficiently thick to avoid rupture during use and generally have a thickness of at least about 0.1 mil. In one preferred embodiment, the membranes are formed by extrusion into thin walled fibers, the overall diameter of which may be up to 75 or more mils, preferably about 1 to 30 mils, with walls having a thickness similar to the flat membrane thickness described above.

The process of this invention can be employed to separate various materials from other ingredients of a fluid feed mixture providing at least one of the materials in the mixture exhibits a complexing rate or transfer rate across the liquid barrier that is greater than at least one other dissimilar or different component of the feedstock. Although the separated material may be quite pure, for instance, of greater than 99% purity, the separation procedure may be used merely to provide a significant increase in the concentration of a given component in a mixture with other components of the feedstock. In the method, the mixture containing the material to be separated may be essentially in the gaseous or vapor phase when in contact with the liquid barrier. The membrane is selectively permeable in the presence of the liquid barrier to the component of the feedstock to be separated. Since there is little, if any, passage for the feedstock across the separation zone except by becoming part of or reacting with the liquid barrier, this liquid barrier controls the selectivity of the liquid barrier-semi-permeable membrane combination. The cuprous ions readily form complexes with the material to be separated upon contact with the feed, and, in addition, the complexes dissociate back to the complex-forming ions and the material to be separated, under the conditions which exist on the discharge side of the liquid barrier and semi-permeable membrane as employed in the process. The released separated material exits the discharge side of the membrane and can be removed from the vicinity of the barrier as by a sweep gas or through the effect of vacuum on this side of the barrier.

Quite advantageously, the system can be used to separate aliphatically-unsaturated hydrocarbons from other hydrocarbons which may be aliphatically saturated or aliphatically-unsaturated, or from non-hydrocarbon materials, including fixed gases such as hydrogen. The feed mixture may thus contain one or more paraffins, including cycloparaffins, mono- or polyolefins, which may be cyclic or acyclic, and acetylenes or alkylenes, and the mixture may include aromatics having such aliphatic configurations in a portion of their structure. Often, the feed mixture contains one or more other hydrocarbons having the same number of carbon atoms as the unsaturated hydrocarbon to be separated or only a one carbon atom difference. Among the materials which may be separated according to this invention are ethylene, propylene, butenes, butadiene, isoprene, acetylene and the like.

Often, the reactivity of aliphatically-unsaturated hydrocarbons with the complex-forming ions in their order of decreasing activity goes from acetylenes or dienes to monoolefins, the aliphatically-saturated hydrocarbons and other materials present being essentially non-reactive. Also, different reactivities may be exhibited among the various members of a given type of aliphatically-unsaturated hydrocarbons. The process can thus be used to separate paraffins from monoolefins; diolefins or acetylenes; diolefins from monoolefins; or acetylenes from paraffins, monoolefins or diolefins; as well as to separate a given aliphatically-unsaturated hydrocarbon from another of such materials in its class where the members have differing complexing rates with or transport rates across the liquid barrier. The feed need only contain a small amount of aliphatically-unsaturated hydrocarbon, as long as the amount is sufficient so that the unsaturated material to be separated selectively reacts with the complex-forming ions to a significant extent, and thus at least one other component of the feed is less reactive or non-reactive with the complex-forming ions.

The aliphatically-unsaturated materials of most interest with regard to separation have 2 to about 8 carbon atoms, preferably 2 to 4 carbon atoms. The separation of aliphatically-unsaturated materials from admixtures containing other gaseous materials, such as the separation of ethylene or propylene from admixtures with other normally gaseous materials, e.g. one or more of ethane, propane, and methane and hydrogen, is of particular importance. Frequently, such feed mixtures for the process contain about 1 to 50 weight percent ethylene, about 0 to 50 weight percent ethane and about 0 to 50 weight percent methane. Another process that may be of special significance is the separation from ethylene of minor amounts of acetylene.

The partial pressure of the aliphatically-unsaturated component of the feed at the input side of the liquid barrier used in the separation is greater than the partial pressure of this unsaturated hydrocarbon on the discharge or exit side of the liquid barrier semi-permeable membrane composite. This pressure drop of the unsaturated hydrocarbon to be separated may often be at least about 0.5 pound per square inch, and is preferably at least about 20 psi, although the pressure drop should not be so great that the liquid barrier is ruptured or otherwise deleteriously affected to a significant extent. Conveniently, the total pressure of the feed is up to about 1000 pounds per square inch. The discharge partial pressure of the unsaturated hydrocarbon can preferably be controlled by subjecting the exit side of the liquid barrier to the action of a sweep gas that may be essentially inert to forming a complex with the complex-forming ions in solution in the liquid barrier. The sweep gas picks up the discharged aliphatically-unsaturated components, and the sweep gas may be selected so that it can be readily separated from the aliphatically-unsaturated hydrocarbon material if that be necessary for the subsequent use of the unsaturated hydrocarbon. Unless a reaction with the separated hydrocarbon is desired, the sweep gas should be relatively inert therewith and may be, for instance, butane, carbon dioxide or the like.

The temperature across the liquid barrier-semipermeable film composite employed in the separation procedure can be essentially constant or it may vary, and decomposition of the metal-unsaturated hydrocarbon complex can be affected primarily by the drop in the partial pressure of the aliphatically-unsaturated hydrocarbon on the exit side of the liquid barrier compared with the partial pressure on the feed side. Conveniently, the temperature of the liquid barrier may be essentially ambient, especially in the case of feedstocks that are gaseous at this temperature and the pressure employed on the feed side of the liquid barrier. The temperature of the liquid barrier may, however, be reduced or elevated from ambient temperature. Often, the temperature may be up to about 100° C., and elevated temperatures may even be desired to put the feedstock in the gaseous or vapor phase. Neither the temperature nor the pressure used should, however, be such as to destroy the difference in transport rate across the liquid barrier, semi-permeable film composite of the aliphatically-unsaturated hydrocarbons whose separation is sought, compared with that of the other components of the feed. The conditions should also not be such that physical disruption of the liquid barrier or any other significant malfunction results.

The methods and products of this invention and their value are shown further by the following examples. Unless otherwise indicated, the percentages given are on a weight basis.

EXAMPLE 1

A complexing solution is prepared as follows:
2.0 Grams of CuCl are placed on a 10 ml. flask and 5 ml. of 4M $NH_4Cl$ solution are added and mixed by shaking. Next, 0.86 ml. of concentrated HCl is then added to the solution and mixed in. The flask is then filled with 4M $NH_4Cl$ solution until the solution is brought up to the 10 ml. mark. A dark brown complexing solution results.

A 0.5 ml. aliquot of the solution is spread on top of two 0.3 mil thick membrane films made of silicon polycarbonate (MEM-213, manufactured by General Electric and sometimes referred to as XD-1) to produce two test membranes designated 1-A and 1-B.

EXAMPLE 2

Another complexing solution is prepared as in Example 1 except that the $NH_4Cl$ solution is a 5M instead of 4M solution. The resulting dark brown solution is applied to two membrane films as in Example 1 to produce two more test membranes designated 2-A and 2-B.

EXAMPLE 3

A complexing solution similar to that of Example 1 is prepared except that 2.0 grams of elemental powdered copper, having a particle size of about 0.6 mils, is added as the reducing agent to the CuCl before the $NH_4Cl$ solution is added to produce a clear solution containing some undissolved copper metal. The solution is applied to a membrane film as in Example 1 to produce a membrane of the present invention designated 3-A.

EXAMPLE 4

A complexing solution similar to that of Example 2 is prepared except that 2.0 grams of elemental powdered copper are added to the CuCl before the $NH_4Cl$ solution is added. The resulting very clear solution containing some undissolved copper metal is applied to a membrane film as in Example 2 to produce another membrane of the present invention designated 4-A.

For testing the membranes of Examples 1 to 4, a closed glass cell is used in which the membrane film is placed so as to divide the cell into an inlet and an outlet side. A gas inlet tube passes through the cap of the cell and extends into the cell ending near the membrane. A tube of larger diameter surrounds the inlet or feed tube forming an annular passage which permits exhaust of those gases which do not permeate the membrane. On the outlet side of the cell and membrane, another annular arrangement is used whereby a purging gas, nitrogen, passes into the outlet side of the cell and sweeps away gases which permeate the membrane. The nitrogen passes in through the smaller tube and carries away the permeated or separated gases through the surrounding annular passage. The test cell is divided into upper and lower compartments locating the membrane horizontally across the cell. The cell internal cross-sectional area is 3.8 cm$^2$ and the cross-section is fully covered by the film membrane in a manner to provide an effective membrane area of 2.2 cm$^2$. The main body of the cell has a height of 41 mm. and a gas outlet at each end. A feed inlet tube enters the upper end of the cell and opens about 5 mm. above the film, and a sweep gas inlet tube enters the lower end of the cell and opens about 1 mm. below the film.

A mixed gas of methane, ethane, ethylene, and acetylene is supplied to the cell at 10 ml./min. under a pressure of 40 psig. This feed gas contains 15.7% $CH_4$, 52.9% $C_2H_4$, 30.1% $C_2H_6$ and 1.26% $C_2H_2$. The permeate through the membrane is purged from the cell with a 10 ml./min. stream of nitrogen. The permeate composition and permeation rate are determined for each film tested. These results are summarized in Table I below.

In conducting the above Examples, it was determined that the CuCl—NH$_4$Cl—HCl complexing solutions are susceptible to oxidation, and contact with oxygen after the solution has been prepared should be minimized and the solution should be kept in constant contact with the reducing agent. Thus, as mentioned above, elemental copper may advantageously be included in the membrane film-forming solutions and/or be combined with the CuCl before or during addition of the NH$_4$Cl solution to retard CuCl degradation. Thus, we prefer not to combine the CuCl with the NH$_4$Cl before the CuCl and elemental copper are combined since such combination may make the system less effective in the separation.

EXAMPLE 5

It is known that cupric chloride-cuprous chloride ionic mixtures are brown in color and that cuprous chloride alone is clear. This is born out by the colors of the solutions prepared by Examples 1–4 above. Thus an easy and reliable means of determining whether or not a particular reducing agent will most effectively stabilize a cuprous copper based, complex-forming liquid barrier constituent is to add a stoichiometric amount or an amount in excess of the stoichiometric amount of reducing agent to the cuprous ion-containing constituent during its preparation. If the resulting solution is clear, then the reducing agent is quite effective. If it is brown or brownish-green, the reducing agent is less effective or has been added in a less effective amount.

This test is used to determine the effectiveness of stannous chloride. A solution is prepared as in Example 1 except that 0.5 gms. of stannous chloride is added to the CuCl before the NH$_4$Cl is added. The resulting solution is clear in color, illustrating that stannous chloride is an effective reducing agent.

TABLE I

ADVANTAGES OF COPPER IN THE PERFORMANCE OF THE CuCl COMPLEXING SOLUTION

Solutions
No. 1 — 2M CuCl + 1M HCl + 4M NH$_4$Cl
No. 2 — 2M CuCl + 1M HCl + 5M NH$_4$Cl
No. 3 — 2M CuCl + 1M HCl + 4M NH$_4$Cl + Copper
No. 4 — 2M CuCl + 1M HCl + 5M NH$_4$Cl + Copper

| Membrane | Solution | Product Analysis | | | | P | $S_{C_2H_4}$*1 | $S_{C_2H_2}$*2 |
| --- | --- | --- | --- | --- | --- | --- | --- | --- |
| | | % CH$_4$ | % C$_2$H$_4$ | % C$_2$H$_6$ | % C$_2$H$_2$ | (ml/cm$^2$min) | | |
| 1-A | No. 1 | .48 | 90.15 | 2.11 | 7.25 | .023 | 30 | 102 |
| 1-B | No. 1 | .46 | 91.71 | .67 | 7.16 | .017 | 70 | 230 |
| 2-A | No. 2 | 1.28 | 88.71 | 1.91 | 8.10 | .003 | 24 | 92 |
| 2-B | No. 2 | .62 | 90.65 | .70 | 8.03 | .006 | 59 | 221 |
| 3-A | No. 3-day 1 | .33 | 91.22 | .77 | 7.67 | .040 | 72 | 253 |
| 3-A | -day 2 | .34 | 91.98 | .36 | 7.33 | .047 | 114 | 381 |
| 4-A | No. 4-day 1 | .35 | 90.89 | .67 | 8.09 | .031 | 77 | 288 |
| 4-A | -day 2 | .40 | 92.37 | .54 | 6.69 | .041 | 85 | 258 |

$$*1 S_{C_2H_4} = \frac{[\% CH_4 + \% C_2H_6] \text{ feed}}{[\% C_2H_4] \text{ feed}} \times \frac{[\% C_2H_4] \text{ product}}{[\% CH_4 + \% C_2H_6] \text{ product}}$$

$$*2 S_{C_2H_2} = \frac{[\% CH_4 + \% C_2H_6] \text{ feed}}{[\% C_2H_2] \text{ feed}} \times \frac{[\% C_2H_2] \text{ product}}{[\% CH_4 + \% C_2H_6] \text{ product}}$$

As shown in Table I, the systems containing the reducing agent (metallic copper) performed satisfactorily in the separation process for the two-day period. The systems without the reducing agent functioned at considerably lower permeabilities, P, and exhibit inferior ethylene selectivity, $S_{C_2H_4}$, and acetylene selectivity, $S_{C_2H_4}$, as compared to the systems of the present invention.

EXAMPLE 6

To show that stannous chloride is effective in regenerating a cuprous ion-containing liquid barrier, a solution is prepared as in Example 1 but with CuCl$_2$ instead of CuCl. The resulting solution is green, indicating that essentially all of the copper ions are Cu$^{++}$. One half of the stoichiometric amount of stannous chloride necessary to reduce the Cu$^{++}$ to Cu$^+$ is added to the solution.

The solution turns to dark brown, indicating that it contains a mixture of $Cu^+$ and $Cu^{++}$ ions. The stannous chloride effectively reduces a substantial amount of cupric ions to complexing cuprous ions.

EXAMPLE 7

A solution is prepared as in Example 6 and twice the stannous chloride (full stoichiometric amount) is added. The solution becomes colorless, indicating that all of the cupric ions are reduced to useful complexing cuprous ions.

EXAMPLE 8

A complexing solution is prepared as follows: 2.0 grams of CuCl are placed in a 10 ml. flask and 2.0 grams of elemental powdered copper having a particle size of about 0.6 mils are added. Next 5 ml. of 4M $NH_4Cl$ solution are added and mixed by shaking, and then 0.86 ml. of concentrated HCl is added and mixed into the solution. The flask is then filled with 4M $NH_4Cl$ solution until the solution is brought up to the 10 ml. mark. A solution results containing some undissolved copper metal therein.

A 0.5 mil. aliquot of the solution is spread on top of 0.3 mil. thick membrane film and the composites are employed in separation processes such as described for the systems of Examples 1 to 4 above, and are subjected to a strong reducing agent to rejuvenate the elemental copper so that system performance is maintained.

It is claimed:

1. A membrane-liquid barrier system comprising a semi-permeable membrane film and an aqueous liquid barrier in contact with said film, said liquid barrier having dissolved therein a complex-forming cuprous ion component and said barrier being in contact with a reducing agent in an amount sufficient to retard oxidation of said cuprous ion component.

2. The membrane of claim 1 wherein said liquid barrier contains from about 2 to about 40% by weight of reducing agent based on the weight of the total solution.

3. The membrane of claim 1 wherein said complex-forming cuprous ion component is a cuprous ion complex which includes ammonium ions.

4. The membrane of claim 3 wherein said cuprous ion complex further includes a mineral acid.

5. The membrane of claim 4 wherein said cuprous ion complex is a cuprous chloride-ammonium chloride-hydrochloric acid complex.

6. The membrane of claim 5 wherein said reducing agent is elemental copper.

7. The membrane of claim 6 wherein said elemental copper is combined with cuprous chloride before or during the addition of ammonium chloride thereto to retard CuCl degradation.

8. The membrane of claim 1 wherein said reducing agent is elemental copper.

9. A membrane-liquid barrier system comprising a semi-permeable, water-soluble membrane film in contact with an aqueous liquid barrier, said aqueous liquid barrier having dissolved therein a complex-forming cuprous ion component which, in the presence of water, provides cations that are capable of forming a complex with aliphatically unsaturated hydrocarbons, and said aqueous liquid barrier being in contact with a reducing agent in an amount sufficient to retard oxidation of said cations.

10. The membrane of claim 9 wherein said aqueous liquid barrier contains from about 2 to about 40% by weight of reducing agent based on the weight of the total solution.

11. The membrane of claim 9 wherein said complex-forming cuprous ion component is a cuprous ion complex which includes ammonium ions.

12. The membrane of claim 11 wherein said cuprous ion complex further includes a mineral acid.

13. The membrane of claim 12 wherein said cuprous ion complex is a cuprous chloride-ammonium chloride-hydrochloric acid complex.

14. The membrane of claim 13 wherein said reducing agent is elemental copper.

15. The membrane of claim 14 wherein said elemental copper is combined with cuprous chloride before or during the addition of ammonium chloride thereto to retard CuCl degradation.

16. In a method for separating a material from a fluid mixture containing said material and at least one other component which comprises contacting said mixture with a first side of an essentially solid, water-insoluble, semi-permeable membrane in contact with an aqueous liquid barrier having dissolved therein a complex-forming cuprous ion component which ions combine with said material to form a water-soluble complex, the partial pressure of said material on a second side of said semi-permeable membrane being sufficiently less than the partial pressure of said material in said mixture to provide separated material on said second side of said semi-permeable membrane, and removing said separated material from the vicinity of said second side of said semi-permeable membrane, the improvement which comprises providing a reducing agent in contact with said aqueous liquid barrier in an amount sufficient to retard oxidation of said ions.

17. The method of claim 16 in which said reducing agent is elemental copper.

18. In a method for separating aliphatically-unsaturated hydrocarbon of 2 to 4 carbon atoms which comprises contacting a vaporous mixture containing said aliphatically-unsaturated hydrocarbon with a first side of an essentially solid, water-insoluble, semi-permeable membrane being permeable to said vaporous mixture in the absence of said aqueous liquid, said liquid barrier having dissolved therein a complex-forming cuprous ion component which ions combine with said unsaturated hydrocarbon to form a water-soluble complex, the partial pressure of said unsaturated hydrocarbon on a second side of said semi-permeable membrane being sufficiently less than the partial pressure of said unsaturated hydrocarbon in said vaporous mixture ot provide separated unsaturated hydrocarbon on said second side of said semi-permeable membrane, and removing separated unsaturated hydrocarbon from the vicinity of said second side of said semi-permeable membrane, the improvement which comprises providing a reducing agent in contact with said aqueous liquid barrier in an amount sufficient to retard oxidation of said ions.

19. The method of claim 18 wherein said aqueous liquid barrier contains from about 2 to about 40% by weight of reducing agent based on the weight of the total solution.

20. The method of claim 18 wherein said complex-forming cuprous ion component is a cuprous ion complex and includes ammonium ions.

21. The method of claim 19 wherein said cuprous ion complex further includes a mineral acid.

22. The method of claim 21 wherein said cuprous ion complex is a cuprous chloride-ammonium chloride-hydrochloric acid complex.

23. The method of claim 22 wherein said reducing agent is elemental copper.

* * * * *

UNITED STATES PATENT OFFICE
CERTIFICATE OF CORRECTION

PATENT NO. : 4,015,955
DATED : April 5, 1977
INVENTOR(S) : Edward F. Steigelmann and Charles S. Sokol It is certified that error appears in the above-identified patent and that said Letters Patent are hereby corrected as shown below:

Column 2, line 13, "separation" should be --separating--.

Column 3, line 28, before "film" insert -- membrane --.

Column 4, line 12, "40%" should be --400%--.

Column 4, line 64, "t-butandol" should be --t-butanol--.

Column 5, line 46, "flim-forming" should be --film-forming--.

Column 5, line 47, "conponent" should be --component--.

Column 6, line 35, "NaBH$_3$CH," should be --NaBH$_3$CN,-- and "Ha$_3$N," should be --Na$_3$N,--.

Column 6, line 39, "membrame-liquid" should be --membrane-liquid--.

Column 7, line 35, "present" should be --pressure--.

Column 7, line 41, after the figure "10", "psi" was omitted.

Column 8, line 11, after the word "aqueous" the word "solution" was omitted.

Column 8, line 41, the word "be" should be --by--.

Column 8, line 63, the word "membrane" should be --medium--.

Column 9, line 21, "polyamide" should be --polyamine--.

UNITED STATES PATENT OFFICE
CERTIFICATE OF CORRECTION

PATENT NO. : 4,015,955
DATED : April 5, 1977
INVENTOR(S) : Edward F. Steigelmann and Charles S. Sokol It is certified that error appears in the above-identified patent and that said Letters Patent are hereby corrected as shown below:

Column 9, line 60, "polyamides" should be --polyamines--.

Column 10, line 16, "2,430,932" should be --2,430,923--.

Column 10, line 22, "15%" should be --50%--.

Column 11, line 6, the word "the" first occurrence, should be --are--.

Column 11, line 33, the word "cross-linked" should be --cross-linking--.

Column 14, line 31, the word "on" should be --in--.

Column 15, line 67, "$SC_2H_4$" should be --$SC_2H_2$--.

Column 17, line 59, the word "water-soluble" should be --water-insoluble--.

Signed and Sealed this

Twenty-eighth Day of June 1977

[SEAL]

Attest:

RUTH C. MASON
Attesting Officer

C. MARSHALL DANN
Commissioner of Patents and Trademarks